United States Patent [19]

Schuss

[11] Patent Number: 4,498,868
[45] Date of Patent: Feb. 12, 1985

[54] DENTAL HAND PIECE

[75] Inventor: Werner Schuss, Heppenheim, Fed. Rep. of Germany

[73] Assignee: Siemens Aktiengesellschaft, Berlin & Munich, Fed. Rep. of Germany

[21] Appl. No.: 398,408

[22] Filed: Jul. 14, 1982

[30] Foreign Application Priority Data

Jul. 29, 1981 [DE] Fed. Rep. of Germany ....... 3129932
May 19, 1982 [DE] Fed. Rep. of Germany ....... 3219017

[51] Int. Cl.³ .............................................. A61C 3/02
[52] U.S. Cl. .................................................... 433/29
[58] Field of Search ........................... 433/29, 99, 126; 356/22, 23, 24; 73/466; 315/241 S

[56] References Cited

U.S. PATENT DOCUMENTS

| | | | |
|---|---|---|---|
| 3,144,584 | 8/1964 | Fiandra et al. | 315/241 S |
| 3,397,457 | 8/1968 | Gosselin . | |
| 3,614,414 | 10/1971 | Gores | 433/29 X |
| 3,625,612 | 12/1971 | Decker, Jr. et al. | 356/24 |
| 3,634,938 | 1/1972 | Hutchinson | 433/29 |
| 3,761,178 | 9/1973 | Turner et al. | 356/24 |
| 4,260,382 | 4/1981 | Thomson | 433/29 X |
| 4,330,274 | 5/1982 | Friedman et al. | 433/29 |

Primary Examiner—Robert P. Swiatek
Attorney, Agent, or Firm—Hill, Van Santen, Steadman & Simpson

[57] ABSTRACT

An improved dental hand piece which has a driven tool which either is rotated or reciprocated and includes an illumination arrangement for projecting light from an exit end at a tip of the tool and the work area includes a stroboscopic device for creating light pulses having a light frequency which coincides with a motion frequency of the tool in such a manner that the surface of the tool is visible during motion. The stroboscopic device can either be a mechanical stroboscope or be a high-speed flash stroboscope.

16 Claims, 13 Drawing Figures

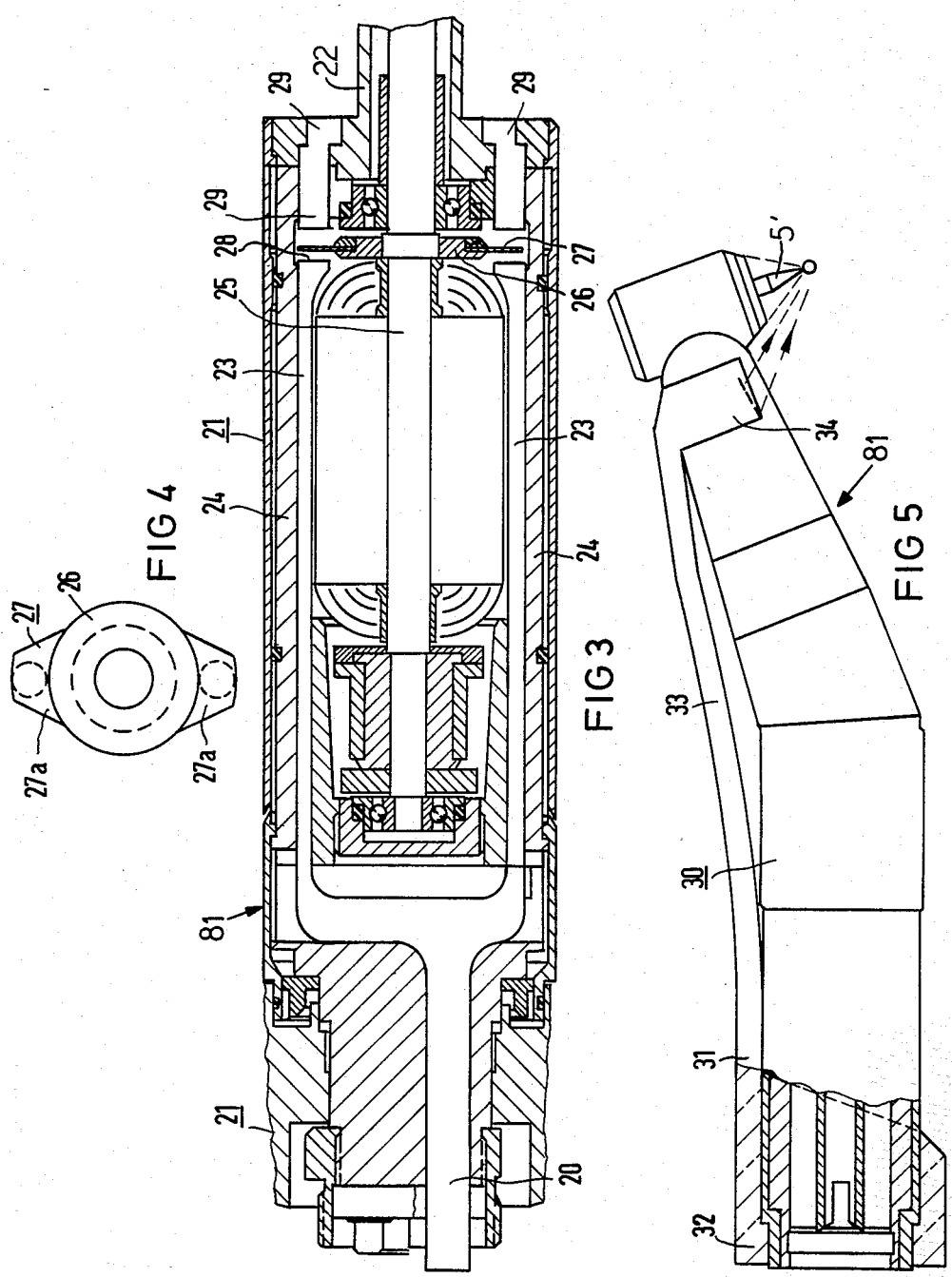

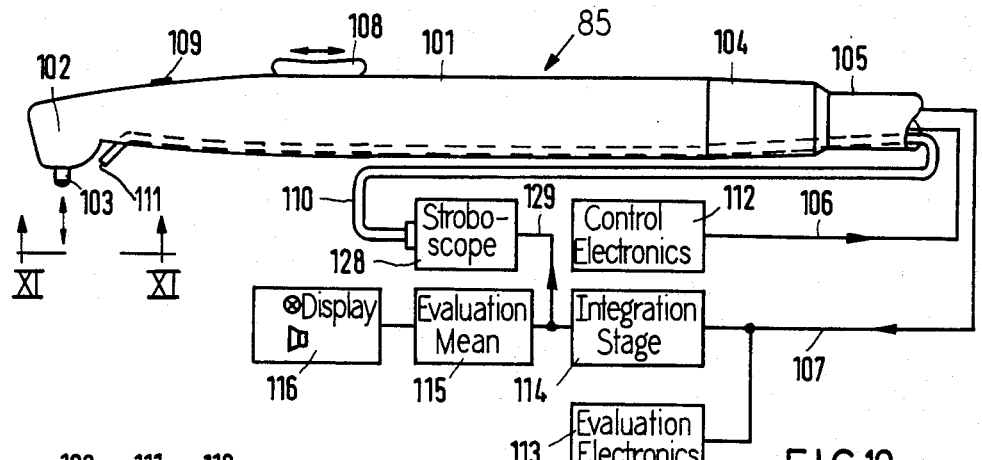
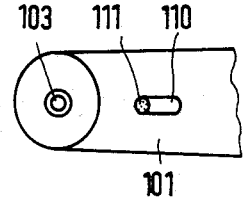
FIG 11
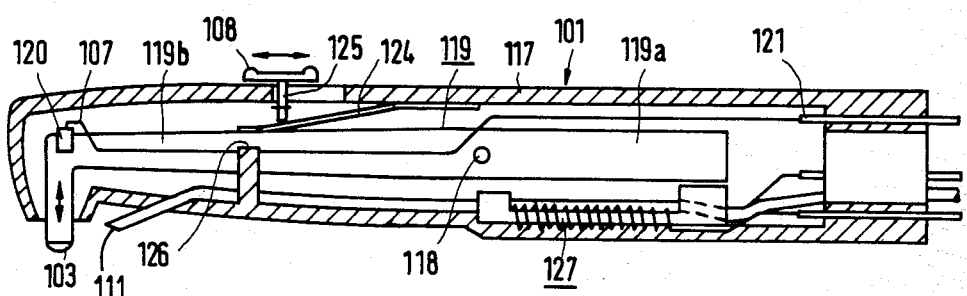
FIG 12

DENTAL HAND PIECE

BACKGROUND OF THE INVENTION

A dental hand piece arrangement which either has a rotating tool or a reciprocating tool and the arrangement includes a drive device for placing the tool in motion and an illumination device which has a light exit end for directing light onto the preparation location adjacent the tip of the tool.

Presently known dental hand pieces, which have a rotating tool such as a drill may utilize either an air turbine for placing the tool in rotation or an electrical motor. In the dental hand piece disclosed in U.S. Pat. Nos. 3,397,475 and 3,634,938, the dental tool is rotated by use of an air-driven turbine and the hand piece is provided with a light conductor which is either disposed within the hand piece or on the outside of the hand piece. The light conductor in either case has an exit end which is adjacent the tool for illuminating the tip of the tool.

Such illumination arrangements, however, serve exclusively for the illumination of the preparation location. In other words, they illuminate the location on which the tool is operating.

SUMMARY OF THE INVENTION

The present invention is concerned with a completely different problem. The present invention is directed to creating an arrangement which allows the tool to be observed during the treatment in order, for example, to either be able to precisely fix the point of emplacement of the tool on the object or be able to determine the blunting and wear of the tool blades at all times. Then the present invention enables replacing a blunt or worn tool, and therefore decreases the chance of an inadmissibly high degree of heating of the preparation location from occurring due to the blunt tool and thus decreases the danger connected therewith of a destruction of the bone tissue or damage to the dental pulp.

In order to achieve these objects, the present invention is directed to an improvement in a dental hand piece arrangement having a housing, a tool mounted in the housing for movement, drive means disposed in the housing for placing the tool in motion with a motion frequency and illumination means for projecting light from an exit end at the tip of the tool. The improvement is that the illumination means includes stroboscopic means for creating light pulses with a light pulse frequency which coincides with the motion frequency of the tool in such a manner that the surface of the tool is visible during motion. Thus, the light pulse frequency and the motion frequency is either a whole multiple or a whole fraction of the motion frequency of the tool which motion frequency may either be a reciprocating motion of a percussion or hammer instrument or a rotating motion of a rotating drill.

As a result of the invention, it is now possible to not only illuminate the preparation location but also to observe the tool surface during the treatment. When the cutting edge or blade becomes blunt or respectively blocked with eroded material, it can be replaced. Advantageously, the device is designed in such a manner that the light pulses proceed synchronously to the movement of the tool so that a standing image of the tool surface is present for observation by the user during the treatment.

The stroboscopic means can be obtained by utilizing a high speed flash stroboscope whose frequency is tuned to that of the motion frequency either manually or by either utilizing sensors to either determine the speed of the motor or drive means and to adjust the stroboscope accordingly or utilizing the drive current to the motor to adjust the stroboscope accordingly. In addition, the stroboscopic means can use a mechanical arrangement for creating the light pulse frequency which can be a rotating shutter in the path of light being conducted to the exit end or a mirror which is rotated relative to an aperture or light pickup surface so that light pulses are projected through the aperture onto the tool or into a light conductor which then projects it at the tool on each rotation of a drive shaft.

BRIEF DESCRIPTION OF THE DRAWINGS

FIG. 3 is a longitudinal cross-sectional view with portions in elevation of the drive portion of a dental hand piece containing a mechanical stroboscopic means;

FIG. 4 is a plan view of the part forming the mechanical stroboscopic means in the device of FIG. 3;

FIG. 5 is a side view with portions broken away for purposes of illustration of a grip part and external light conductor in a coupling arrangement for coupling to the drive part of the dental hand piece of FIG. 3;

FIG. 10 is a plan view of a dental hand piece having a reciprocating tool schematically illustrating the controls for the tool and the stroboscopic means in accordance with the present invention;

FIG. 11 is a partial view taken along the lines XI—XI of FIG. 10; and

FIG. 12 is a longitudinal cross-sectional view of the dental hand piece arrangement of FIG. 10.

DESCRIPTION OF THE PREFERRED EMBODIMENTS

Figure 1:
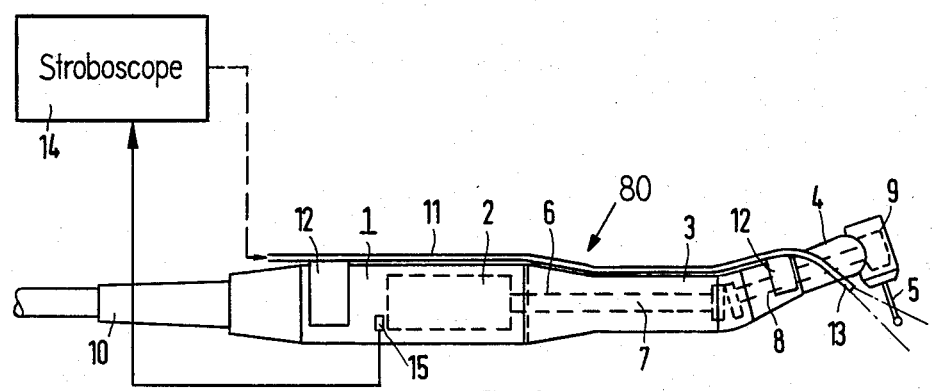
FIG. 1 is a side view of a dental hand piece having an electric motor and illumination means which is illustrated schematically as an external stroboscope.

The principles of the present invention particularly useful when incorporated into a dental hand piece and generally indicated at 80 in FIG. 1. The dental hand piece 80 includes a drive unit or part 1, which has an electric motor 2 with a drive shaft 6. In addition, the hand piece 80 has a gripping sleeve or portion 3 which terminates in a head part 4 which has a rotatable socket 9 for supporting a tool 5 such as a drill or milling cutter for rotation in a conventional manner. To transmit the rotational motion from the drive shaft 6 of the motor 2 to the socket 9, a drive train composed of drive shafts or sections 7 and 8 extend through the grip sleeve or portion 3 and the head part 4. To supply electrical energy for the motor 2 and also any cooling agent such as air and water, a supply hose 10 is connected to the drive part or portion 1 in a conventional manner.

A light conductor 11 is illustrated as being removably mounted on the outside of the dental hand piece 80 by the assistance of clamps such as 12. The light conductor 11 has a free end or exit end 13 which is directed toward the surface of the tool 5 in order to be able during preparation to illuminate both the preparation location itself as well as the surface of the tool. The other end of the light conductor 11 is illustrated schematically as being conducted to a high speed flash stroboscope 14 which creates a plurality of light pulses at a light pulse frequency and can be a conventional stroboscopic device. The output of the stroboscope 14 can be connected to the light conductor 11 through a separate line, which is either on the outside of the dental hand piece as schematically illustrated or is integrated into the supply hose 10.

The stroboscope 14 can be controlled by a manual setting but is preferably controlled as a function of the rotary frequency of the motor by means of a generator or disciminating element 15 which, for example, can be a field plate or a reflection light barrier that is disposed in the proximity of the armature of the electric motor 2. Thus, the stroboscope 14 can be directly driven with periodic voltage pulses obtainable, for example, with the field plate as schematically illustrated in FIG. 1. Since the high speed flash stroboscope 14 can be of a commercially available type, a matching need only occur at the output to the particular light conductor 11.

Figure 2:
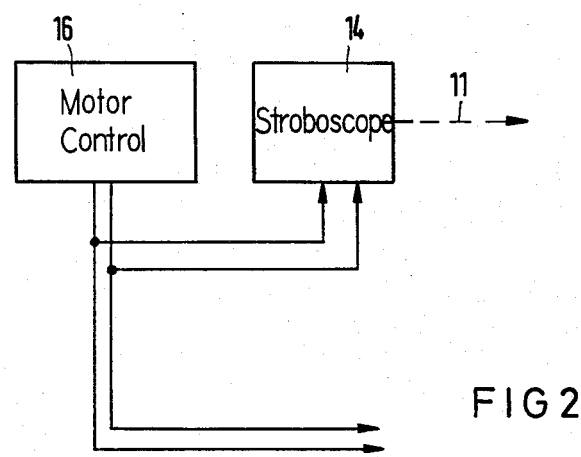
FIG. 2 is a schematic illustration of a speed-dependent control for a stroboscope.

Another type of speed dependent control of a high speed flashing stroboscope is illustrated schematically in FIG. 2. The reference magnitude here is the motor voltage which is branched off the output of the control electronic or motor control 16 which is known per se and controls the drive motor. This branched-off motor voltage then supplies a control signal to the high speed flashing stroboscope 14 whose output is then connected into the conductor 11.

An embodiment of the hand piece in accordance with the present invention is generally indicated at 81 and illustrated in FIGS. 3, 4 and 5. In the hand piece 81, light conductors are conducted in the interior of a drive unit 21 and the stroboscopic means is a mechanical stroboscopic device. Since the structure of the drive motor is sufficiently known, only a few of the parts which are essential concerning the guidance of the light conductor shall be described in detail.

In the hand piece 81, the light from an external source is fed in by a fiber optical light conductor 20 which has a circular cross-section and which splits adjacent the rear of the drive part 21 into two solid glass rods 23 which are offset at 180° to each other. The two glass rods 23 are disposed between the magnet shells 24 of the stator and terminate in circular end surfaces 28.

The mechanical stroboscopic device includes a disk 26 which is secured on an armature shaft 25 of the motor. The disk 26 supports a PVC foil lamina 27 which has a pair of diametrically opposed projections 27a as best illustrated in FIG. 4. The disk 26 with the foil 27 having the projections 27a forms a rotating diaphragm or shutter which rotates between the two end surfaces 28 of the glass rods 23 and two additional correspondingly disposed glass rods 29,29 which have a circular cross-section. This rotating disk with the gap between the end surface 28 and the ends of the additional rods 29 forms the mechanical stroboscopic means. The disk 26 with the plastic foil 27 can be assembled on the shaft 25 as the armature is assembled on the shaft outside of the stator housing. When the armature is inserted into the stator housing, the lamina, as a result of its elasticity, will adapt to the spatial conditions and will assume the desired position between the surfaces 28 and the end of the glass rod 29 automatically during the initial rotation of the armature.

The hand piece 81 includes a gripping sleeve and head part or unit 30 which is mounted for rotation on a mounting or clamping device 22 of the drive part 21 and is best illustrated in FIG. 5. Since the gripping sleeve and head part 30 are rotatable relative to the drive part or unit 21, a transfer part of the light conductor at the end of the gripping sleeve is designated by a light collecting annular ring 32 which tapers and terminates into a conductor 33 at a point 31. The conductor 33 has a circular cross-section and can be formed either of a bundle of fibers or of a single glass rod. The light exit location 34 of the conductor 33 is designed in such a manner that as illustrated by the arrows, light is directed at the active tool surface of a tool 5' which surface is formed by cutters or blades.

When the speed of the tool is near or entirely coincides with the flash or light pulse frequency or is a whole multiple or respectively a whole fraction thereof, the tool surface of the tool 5', particularly cutter surfaces of a drill or miller, becomes clearly visible due to the stroboscopic effect. During the treatment, thus, both the treatment area as well as the drill or tool 5' can be observed. Thus, a clogging of the cutter surfaces or a dulling of these surfaces, which will create heating which may damage the tooth material, can be perceived in time and prevented.

In the above described embodiment, it is assumed that a stepped-down gearing or stepped-up gearing usually present between the drive motor and the tool are approximately or exactly a whole multiple or, respectively, a whole fraction of the motor speed. Thus, a standing image of the tool surface can be seen at the tool when it rotates.

Figure 6:
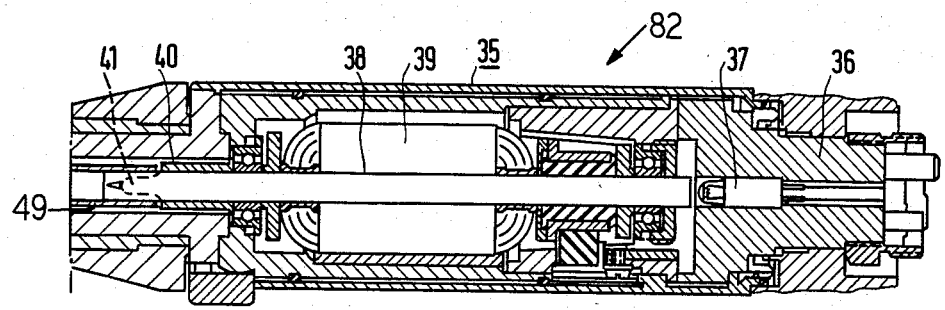
FIG. 6 is a longitudinal cross-sectional view with portions in elevation for purposes of illustration of a drive portion of an embodiment of a dental hand piece in accordance with the present invention.
Figure 7:
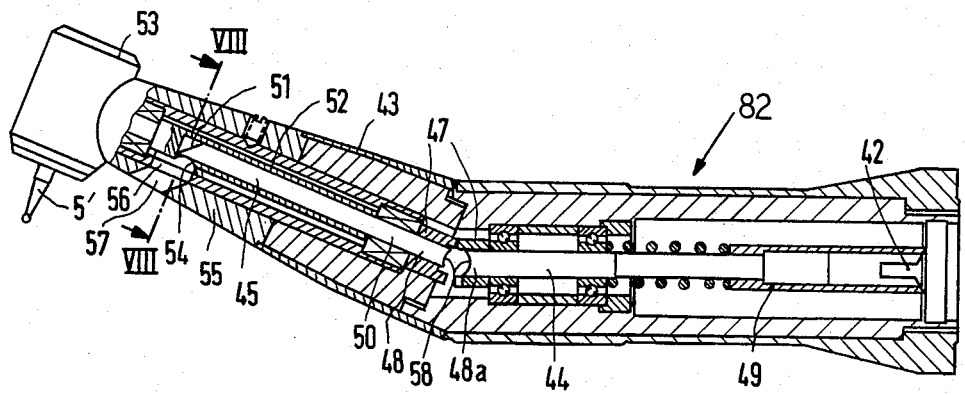
FIG. 7 is a longitudinal cross-sectional view of the grip portion with portions in elevation for purposes of illustration for use with the drive part of FIG. 6 and illustrating a mechanical stroboscopic means.
Figure 7A:
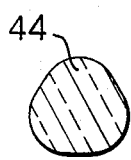
FIG. 7a is a cross-sectional view of a drive shaft in the part of FIG. 7.
Figure 8:
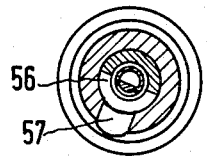
FIG. 8 is a cross-sectional view taken along the lines VIII—VIII of FIG. 7.

Another embodiment of dental hand piece is generally indicated 82 in FIGS. 6 and 7 and includes a drive part or unit 35 (FIG. 6) and a grip sleeve and head unit or part 43 (FIG. 7). In this embodiment, the drive part 35 has a filament bulb 37 mounted in a centrally disposed bore adjacent the connection part 36 which is connected to the supply hose. This bulb 37 is supplied with electrical energy in a known manner through conductors carried in the supply hose. A drive shaft 38 of a motor armature 39 consists of a glass rod with a circular cross-section. One end of the shaft 38 is positioned adjacent the filament bulb 37 and a sleeve 40 is secured at the other end and has dogs such as 41 which when the grip sleeve and head part 43 are connected to the drive unit 37, the dogs 41 are engaged in correspondingly designed coupling elements or grooves 42 of a sleeve 49. The grip sleeve and head part 43 have drive shaft sections 44 and 45 which are mounted in bearings for rotation. These drive shaft sections 44 and 45 may be tubular members which contain glass rods or they may be glass rods with a polygon cross-section with the flat surfaces connected by rounded corners as best illustrated in FIG. 7a. An advantage of utilizing glass rods having a polygon cross-section is that the parts such as sleeve-shaped coupling elements 49 or tooth gears 47 can be secured in place without twisting and without requiring any pinning. The glass rod 44 has an end 48a while the glass rod 45 has an end 48 and each end has a convex end surface 58. As illustrated, the rods are mounted with their axes extending at an angle to each other and these convex end surfaces 58 act to focus the light at the point of intersection of the two drive shaft axes. The drive shaft 45 is composed of a glass rod 50 which is pressed into a metal sleeve 52, which metal sleeve 52 has a projection that extends into driving connection with the socket or drive shaft in the head 53 of the part. The glass rod 50 terminates with an end face 51 which extends at an angle 45° to the axis of the drive shaft. Thus, light will emerge or be reflected by the end face 51 at right angles to the axis to pass through a bore or opening 54 in the sleeve 52. The light emerging from the sleeve is collected in a light pickup surface of a collecting segment 56 which is mounted in a neck part 55 and has a semicircular configuration as best illustrated in FIG. 8. From the collecting element 56, the light will exit through an exit end 57 to be projected on the surface of the tool 5'.

Figure 9:
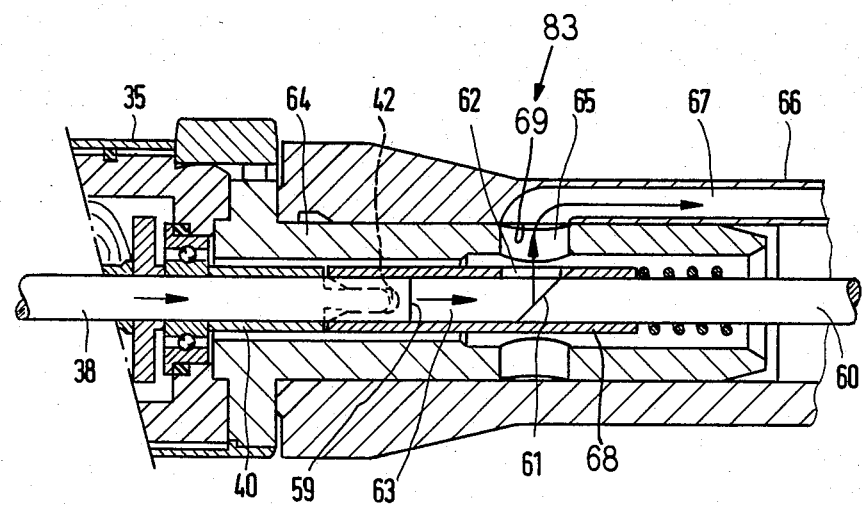
FIG. 9 is a cross-sectional view with portions in elevation of another embodiment of a mechanical stroboscopic means in a portion of a dental hand piece.

Another embodiment of the dental hand piece in accordance with the present invention is generally indicated at 83 in FIG. 9. In this embodiment, the stroboscopic means is not disposed in a neck part of the hand piece 83 but rather is directly positioned at the coupling location between a drive part or unit 35 and the grip sleeve 66. The drive part or unit 35 is substantially the same construction as the unit 35 of FIG. 6 and has a drive shaft 38 which consists of a glass rod having an end face 59 and on which a sleeve 40 having dogs is positioned. The dogs of the sleeve 40 are engaged in grooves or slots 42 of a sleeve 68 which is connected on the drive shaft 60 of the grip sleeve 66. The drive shaft 60 comprises a metal rod such as a steel rod and has an obliquely cut end surface 61 which extends at an angle of 45° to the axis of the shaft 60 and which surface 61 has been polished to be a mirror surface. The sleeve 68 has an opening 62 which is adjacent the end surface 61 on the shaft 60. A space 63 between the end surface 61 and surface 59 of the glass rod 38 can either provide an air path or be filled with an additional glass body.

A connecting or coupling sleeve 64 of the drive part 35 which telescopically recieves the grip part 66 has a plurality of bores or openings 65 which extend at right angles to the axis of the sleeve. Thus, light traveling in the rod 38 is reflected at right angles to the axis of the rod by the mirror formed by the end surface 61 through an opening 65 when it is aligned therewith. The grip sleeve 66 has a light conductor 67 which extends up to the head part and has an exit end such as the exit end illustrated in FIGS. 5 and 7. The light conductor 67 has an input end or light pickup surface 69 which is aligned with one of the bores 65 so that light projected through the bore or opening 65 is received into the light conductor. Since the delivery of light in the hand piece 83 occurs by means of only one light conductor 67 which is aligned with only a single bore 65 of the sleeve 64, a rotational frequency, which corresponds to the drive speed, will occur. When one wishes to have twice the rotational frequency, then two delivery locations are offset at 180° relative to each other and the additional location is also provided with a light conductor.

In the disclosed embodiments, it is presumed that a stepped-down or stepped-up gear present between the drive motor and the tools is nearly or respectively exactly whole multiples or respectively whole fractions of the motor speed in order that the given rotation of the tool which is the movement frequency will coincide with the frequency of the light pulses to obtain a standing image of the tool surface at the tool or an image which runs slightly in the one or the other direction of rotation. Insofar as the gear gradation is not suitable for this purpose, it is conceivable to also dispose the stroboscopic means in the head housing. Such an arrangement is particularly advantageous for turbine hand pieces.

The described stroboscopic means is not limited for rotating tools. On the contrary, it can also be advantageously applied to tools which reciprocate back and forth. A particular advantage is seen in the so-called percussion instrument which exhibits a reciprocating probe as a tool which is struck against a test specimen, for example, against a tooth by means of a magnetically actuated drive. According to the described stroboscopic effect, the point of the probe can appear stationary to the user whereby the aim at the desired location on the subject to be tested can be facilitated. A sample embodiment of such an instrument is illustrated and generally indicated at 85 in FIGS. 10 through 12.

The percussion instrument or hand piece 85 has an oblong handle 101 which merges into a head housing 102 that is at a front and angled end. A tool serving as a probe 103 projects through an end face of the housing 102. A supply hose 105, which contains leads 106 and 107 for a circuit arrangement which will be described hereinafter in greater detail, is connected by means of a connection piece 104 to the other end of the handle 101. The handle 101 also has a manually actuated slide 108 and a display lamp 109.

The instrument 85 also has a light conductor 110 which extends through the hose 105 from a source 128 through the interior of the handle 101 to an exit end 111 which is adjacent the end housing 102. Light which is focused by the exit end 111 is focused in such a manner that it is directed and focused on the tool 103 mainly in the form of a circular light spot in the plane perpendicular to the longitudinal axis of the tool 103 and parallel to the end face of the head housing 102.

The lead 106 is connected to a control electronics 112 which periodically supplies current pulses to a drive disposed in the interior of the handle 101. This current pulse causes a periodic back and forth reciprocating movement motion of the tool 103 as indicated by the double-headed arrow. The line 107 is connected to an acceleration pickup 120 (FIG. 12) and carries an acceleration signal obtained from the tool 103 when it strikes the subject to be tested to an evaluation electronics 113 for further subject-associated evaluation and is also converted into a velocity signal in an integration stage 114 according to the relationship $v = \int b dt$, are further processed in a measuring and evaluation means 115. The means 115 is connected to a display which provides the user with acoustical or optical information.

As best illustrated in FIG. 12, an elongated oscillating lever 119, which supports the tool 103 is mounted for movement in the housing 117 of the handle 101 by an axle bearing 118 which extends at right angles relative to the longitudinal axis of the instrument. The bearing 118 engages the center of gravity of the oscillating lever by means of a nearly friction-free bearing arrangement such as ball-bearings and the bearing 118 divides the lever 119 into a back section 119a and into a front section 119b on which the tool 103 is mounted. Relative to the oscillating lever 119, the test head or tool 103 is angled off at nearly 90° and is designed with a crown adjacent its front end. In comparison to the back section 119a, the oscillating section 119b is designed relatively long as a result of which the test head 103 describes a nearly straight line movement in the direction of the arrow and has a stroke in a range of 2-8 mm.

The acceleration pickup 120, which is secured to the tool 103, is connected to the line 107 which is secured to the oscillating lever 119 at least up to about the bearing 118. The line 107 is connected out of the path of the movable oscillating lever in the direct proximity of this bearing to be connected to a connecting element 121 disposed on the opposite end of the housing 117.

A leaf spring 124 secured to the housing element 117 is provided as a part of a drive for the oscillating lever 119. The leaf spring 124 presses against the oscillating lever section 119b and the amount of pressure is determined by a press pin 125 that is secured on the slide 108. Thus, the spring 124 will urge the lever as illustrated in FIG. 12 in a counter-clockwise direction on the bearing 118. The actual amount of movement in the counter-clockwise direction is limited by a detent 126, which detent 126 is disposed in the housing adjacent a side of the oscillating lever and catches the spring 124 to decouple the spring from the lever. The oscillating lever then continues to move in a free flight free of any forces and with a constant velocity until it strikes against a test subject or against a final detent. The return of the oscillating lever 119 to its initial position occurs by means of an electromagnet 127 which is advantageously disposed corresponding with the oscillating lever section 119a. This magnet 127 is driven by current pulses from the control electronics 112 that are received on a line 106. It should be noted that the leaf spring 124 can be prestressed to different spring tensions by means of the slide 108. Thus, the velocity of the oscillation lever can be influenced by changing the position of the slide 108.

The light conductor 110 as shown in FIG. 12 is largely disposed in the instrument housing 117 and as can be seen from FIG. 10 is connected to a supply source 128 which is outside of the instrument. Supply source 128 is a commercially available high speed flash stroboscope whose flash repetition rate is variable. To drive the high speed flash stroboscope 128, a line 129 is connected to the output of the integration stage 114. Thus, the stroboscope is driven as a function of the velocity of the tool 103 and as a result of which the light pulse frequency proceeds synchronously to the reciprocating movement of the tool. During the movement phase, a standing image of the tool is always present for viewing by the user.

Instead of putting the light conductor 110 on the inside of the housing, it can be removably mounted on the outer surface of the housing by utilizing clamps such as clamp 12 illustrated in FIG. 1.

Although various minor modifications may be suggested by those versed in the art, it should be understood that I wish to embody within the scope of the patent granted hereon, all such modifications as reasonably and properly come within the scope of my contribution to the art.

I claim:

1. In a dental hand piece arrangement having a housing, a tool mounted in the housing for movement, drive means disposed in the housing for placing the tool in motion with a motion frequency, said dirve means including a drive motor and a drive train of at least one drive shaft, said drive train being coupled to the tool to rotate the tool, and illumination means having an exit end mounted adjacent the tool for projecting light from the exit end at a tip of the tool, the improvements comprising said illumination means including a stroboscopic means for creating light pulses having a light pulse frequency which coincides with the motion frequency of the tool in such a manner that the surface of the tool is visible during motion, said stroboscopic means comprising a stroboscopic diaphragm mounted on a drive shaft and the illumination means including at least one light conductor having a gap receiving said diaphragm.

2. In a dental hand piece according to claim 1, wherein the stroboscopic diaphragm is mounted directly on the shaft of the motor and consists of a carrier disk supporting a plastic lamina having at least one portion projecting past the periphery of the disk into said gap.

3. In a dental hand piece according to claim 2, wherein the motor is an electric motor having a permanent magnetic shell as the stator, said light conductors being disposed to extend between said magnetic shells and said gap being adjacent said shells.

4. In a dental hand piece according to claim 3, wherein a pair of light conductors are disposed in the motor, each light conductor at each gap having a circular cross-section, a grip section being mounted on the drive motor unit for relative rotation, said grip section having an annular light collecting ring for receiving light from the light conductors in said drive unit, said annular ring channeling the light from said light conductors to a light conductor extending from said ring to said exit end.

5. In a dental hand piece arrangement having a housing, a tool mounted in a socket for rotation in the housing, drive means disposed in the housing for placing the socket and tool in rotation with a motion frequency, said drive means including a drive motor having a drive shaft, and drive shaft sections connecting the drive shaft of the motor to the socket to rotate the socket and tool, and illumination means having an exit end mounted adjacent the tool for projecting light from the exit end at a tip of the tool, the improvements comprising said illumination means including at least one of said shaft sections and drive shaft being a light conducting shaft, said illumination means including a stroboscopic means for creating light pulses having a light pulse frequency which coincides with the motion frequency of the tool in such a manner that the surface of the tool is visible during motion, and said stroboscopic means comprising means for decoupling light from the light conducting shaft.

6. In a dental hand piece according to claim 5, wherein said drive shaft of the motor and at least one drive shaft section are glass rods, at least one of said glass rods having a non-circular cross-section to enable torque transmission from said rod to an element secured thereon, the ends of the glass rods of two aligned shaft sections being shaped ends for transmitting light therebetween, said stroboscopic means being formed by the coaction of means for reflecting the light from one of said rotating glass rods and light pickup surfaces being disposed on a non-rotating part.

7. A dental hand piece according to claim 6, wherein the number of light pickup surfaces of the non-rotatable hand piece part determines the light pulse frequency.

8. A dental hand piece according to claim 6, wherein the stroboscopic means is disposed in the gripping and head part of the dental hand piece and comprises the last light-conducting rod being secured to a sleeve member having an aperture, said rod having means forming a mirror for projecting light through said aperture, a light-conducting element being provided in a non-rotatable part and extending from the light pickup surface to the exit end.

9. In a dental hand piece according to claim 8, wherein the light pickup surface of the light collecting element extends over half the circumferential angle of movement of said sleeve.

10. In a dental hand piece according to claim 6, wherein at least two drive shaft sections contain light conductors, said two drive shaft sections having an axis inclined at an angle relative to one another and said end faces of the glass rods having a convex shape for focusing the light at a point of intersection of said axes.

11. A dental hand piece according to claim 6, wherein each of the glass rods having a non-circular cross-section of a polygon of three sides connected by rounded corners.

12. In a dental hand piece according to claim 6, wherein a light source is connected adjacent to the drive motor for coupling light into the drive shaft of said motor.

13. In a dental hand piece according to claim 5, wherein the drive shaft of the drive motor terminates in a member having a dog, said dog coacting with an element formed in a sleeve secured on a drive section of the grip portion, said drive section being a metal rod having an end polished to form a mirror extending at an angle to the axis of said rod, said sleeve having a light exit opening aligned with the angle of reflection of said mirror end surface, and a non-rotatable part concentrically arranged to said drive part having at least one light pickup surface receiving light reflected by said end surface, each light pickup surface being connected to a conductor extending to said exit end, the number of said pickup surfaces determining the light pulse frequency.

14. In a dental hand piece according to claim 13, wherein the non-rotatable part is rotatably mounted on a mounting sleeve member of a drive unit of said hand piece, said mounting sleeve member having an opening coacting with the pickup surface to enable light pulses to be coupled into the grip part regardless of the angular position of the grip part on said mounting sleeve member.

15. In a dental hand piece arrangement having a housing, a tool mounted in the housing for movement, drive means disposed in the housing for placing the tool in motion with a motion frequency, and illumination means having an exit end mounted adjacent the tool for projecting light from the exit end at a tip of the tool, the improvements comprising said illumination means including a stroboscopic means for creating light pulses having a light pulse frequency which coincides with the motion frequency of the tool in such a manner that the surface of the tool is visible during motion, said stroboscopic means including a high-speed flash stroboscope and a motion-detecting discriminating element being disposed in the hand piece to determine the speed of movement of the tool, said discriminating element driveing the stroboscope with a velocity signal gained from the detected motion.

16. In a dental hand piece arrangement having a housing, a reciprocating tool being mounted in the housing for reciprocating movement, drive means disposed in the housing for placing the tool in motion with a motion frequency, and illumination means having an exit end mounted adjacent the tool for projecting light from the exit end at a tip of the tool, the improvements comprising said illumination means including a stroboscropic means for creating light pulses having a light pulse frequency which concides with the motion frequency of the reciprocating tool in such a manner that the surface of the tool is visible during motion, and means for measuring acceleration being disposed in a housing on said reciprocating tool, said means for measuring acceleration being connected to integration means for converting acceleration signals into velocity signals, and said stroboscopic means being a high-speed flash stroboscope receiving control pulses from said integration means for determining the light pulse frequency of the stroboscope.

* * * * *